(12) United States Patent
Matsubara

(10) Patent No.: US 10,214,717 B2
(45) Date of Patent: Feb. 26, 2019

(54) CELL DETERMINATION DEVICE, CELL DETERMINATION METHOD, AND CELL DETERMINATION PROGRAM

(71) Applicant: FUJIFILM Corporation, Tokyo (JP)

(72) Inventor: Kenta Matsubara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/362,173

(22) Filed: Nov. 28, 2016

(65) Prior Publication Data

US 2017/0073630 A1   Mar. 16, 2017

Related U.S. Application Data

(63) Continuation of application No. PCT/JP2015/063711, filed on May 13, 2015.

(30) Foreign Application Priority Data

May 30, 2014   (JP) .................................. 2014-112133

(51) Int. Cl.
*C12M 1/34* (2006.01)
*G01N 33/483* (2006.01)
(Continued)

(52) U.S. Cl.
CPC .............. *C12M 41/46* (2013.01); *C12M 1/34* (2013.01); *G01N 33/4833* (2013.01);
(Continued)

(58) Field of Classification Search
CPC ..... C21M 1/34; C12M 41/46; G01N 33/4833; G06K 9/00134; G06K 9/00127; G06T 7/0012; G06T 2207/30242
See application file for complete search history.

(56) References Cited

U.S. PATENT DOCUMENTS

| 2010/0208960 A1 | 8/2010 | Kiyota |
| 2012/0122143 A1 | 5/2012 | Mimura et al. |
| 2012/0134571 A1 | 5/2012 | Ito et al. |

FOREIGN PATENT DOCUMENTS

| JP | 2013-39113 A | 2/2013 |
| WO | WO 2009/031283 A1 | 3/2009 |
| WO | WO 2011/013319 A1 | 2/2011 |

OTHER PUBLICATIONS

Bahnson et al., "Automated Measurement of Cell Motility and Proliferation," BMC Cell Biology, vol. 6, No. 1, Apr. 14, 2005, 27 pages, XP021001254.

(Continued)

*Primary Examiner* — Edward Park
(74) *Attorney, Agent, or Firm* — Birch, Stewart, Kolasch & Birch, LLP

(57) ABSTRACT

Disclosed are a cell determination device, a cell determination method, and a non-transitory computer readable recording medium recorded with a cell determination program capable of objectively determining a state of a cell with high accuracy. The cell determination device includes: a cell information acquisition unit 31 that acquires information relating to a proliferation rate of a cell and information relating to a movement distance of the cell per unit time based on plural cell images obtained by imaging the cell in a time series manner; and a determination unit 32 that determines a state of the cell based on the information relating to the proliferation rate and the information relating to the movement distance.

19 Claims, 8 Drawing Sheets

(51) Int. Cl.
G06K 9/00 (2006.01)
G06T 7/00 (2017.01)
G01N 15/14 (2006.01)

(52) U.S. Cl.
CPC ........ *G06K 9/00134* (2013.01); *G06T 7/0012* (2013.01); *G01N 15/1463* (2013.01); *G06K 9/00127* (2013.01); *G06T 2207/30242* (2013.01)

(56) References Cited

OTHER PUBLICATIONS

Deasy et al., "Tracking Stem Cell Function with Computers Via Live Cell Imaging: Identifying Donor Variability in Human Stem Cells," Oper Tech Orthop, vol. 20, No. 2, 2010 (Jun. 1, 2010), pp. 127-135, XP055364384.

Dewan et al., "Tracking Biological Cells in Time-Lapse Microscopy: An Adaptive Technique Combining Motion and Topological Features," IEEE Transactions on Biomedical Engineering, vol. 58, No. 6, Jun. 1, 2011, pp. 1637-1647, XP011408390.

Extended European Search Report, dated Apr. 28, 2017, for corresponding European Application No. 15799020.1.

Japanese Office Action, dated Jul. 11, 2017, for corresponding Japanese Application No. 2014-112133, with an English translation.

International Search Report issued in PCT/JP2015/063711, dated Aug. 18, 2015.

Written Opinion of the lnternationai Searching Authority issued in PCT/JP2015/063711 (PCT/ISA/237), dated Aug. 18, 2015.

English translation of Written Opinion of the International Searching Authority issued in PCT/JP2015/063711 (PCT/ISA/237), dated Aug. 18, 2015.

Japanese Decision of Refusal for counterpart Japanese Application No. 2014-112133, dated Dec. 5, 2017, including an English machine translation.

Extended European Search Report, dated Mar. 8, 2018, for European Application No. 17203065.2.

CELL DETERMINATION DEVICE, CELL DETERMINATION METHOD, AND CELL DETERMINATION PROGRAM

CROSS-REFERENCE TO RELATED APPLICATIONS

This application is a Continuation of PCT International Application No. PCT/JP2015/063711 filed on May 13, 2015, which claims priority under 35 U.S.C. § 119(a) to Japanese Patent Application No. 2014-112133 filed on May 30, 2014. Each of the above application(s) is hereby expressly incorporated by reference, in its entirety, into the present application.

BACKGROUND OF THE INVENTION

1. Field of the Invention

The present invention relates to a cell determination device, a cell determination method, and a non-transitory computer readable recording medium recorded with a cell determination program that determine a state of a cell based on plural images obtained by imaging a cell in a time series manner.

2. Description of the Related Art

A stem cell such as an ES cell or an iPS cell has an ability to be differentiated into cells of various tissues, and is attracting attention as a cell capable of being applied in regenerative medicine, drug development, disease elucidation, or the like.

A stem cell is seeded in a scaffolding member (culture bed) in a culture vessel set in a cell culture device, and is proliferated on the scaffolding member using a culture medium (culture solution) as a nutrient. The proliferated stem cells grow as a stem cell colony while repeating dense binding.

In a growth process of stem cells, since it is extremely difficult to make stem cells that have started differentiating into a specific tissue once change and grow into a different tissue in the middle of the process, it is important to proliferate a stem cell up to a sufficient number of cells while maintaining an undifferentiated state and to differentiate the stem cells to cells of a desired tissue in a subsequent process from the viewpoint of productivity.

Further, only a region having a highly undifferentiated characteristic in a stem cell colony may be cut out and transplanted in a separate culture vessel for carrying out subculture, but it is necessary to extract only an undifferentiated stem cell during the subculture. That is, in culturing a stem cell, it is necessary to appropriately determine differentiation and undifferentiation of the stem cell.

Further, with respect to determination of a state of a cell, a method of culturing a cancer cell extracted from a human body and determining the degree of malignancy of the cancer cell has been used. The determination of the degree of malignancy of a cancer cell is important for the determination of a cancer treatment policy of a patient. That is, it is important to appropriately determine the degree of malignancy of a cancer cell.

SUMMARY OF THE INVENTION

Here, the above-mentioned determination of the state relating to the differentiation and undifferentiation of the stem cell or the degree of malignancy of the cancer cell has been performed by visual observation of a culture expert or by automatically determining the cell colony or shapes of individual cells based on a still image of the cell.

However, in the visual observation, an irregularity may occur in the determination according to the proficiency of an observer. Further, in the automatic determination using the still image, for example, in the case of a still image shown in FIG. 8, it may be determined that a portion indicated by an arrow A has a highly undifferentiated characteristic from a density or shapes of cells, and it may be determined that a portion indicated by an arrow C has a high differentiation characteristic. However, in a portion indicated by an arrow B, it is not possible to clearly distinguish a density or shapes of cells, and it may not be possible to perform an appropriate state determination.

Furthermore, JP2013-39113A has proposed a method for calculating a movement amount of a cell based on plural images obtained by imaging a cell in a time series manner and determining the degree of differentiation of a cell from a stem cell based on the movement amount.

However, when the state of the cell is determined by only the movement amount of the cell as disclosed in JP2013-39113A, erroneous determination may occur. For example, there may be a case where undifferentiated cells and differentiated cells are present together. Generally, it may be assumed that as a movement amount of a cell becomes larger, differentiation is further progressed. However, in a case where the degree of differentiation is determined from an average of movement amounts of cells, if the small number of differentiated cells of which movement amounts are excessively large exist, it may be determined that the degree of differentiation is progressed even in a case where most cells are undifferentiated cells, and in this case, the degree of differentiation cannot be appropriately determined.

In view of the above-mentioned problems, an object of the invention is to provide a cell determination device, a cell determination method, and a non-transitory computer readable recording medium recorded with a cell determination program capable of objectively determining a state of a cell with high accuracy.

According to the invention, there is provided a cell determination device comprising: a cell information acquisition unit that acquires information relating to a proliferation rate of a cell and information relating to a movement distance of the cell per unit time based on a plurality of cell images obtained by imaging the cell in a time series manner; and a determination unit that determines a state of the cell based on the information relating to the proliferation rate and the information relating to the movement distance.

In the cell determination device according to the invention, the determination unit may determine the degree of differentiation or the degree of malignancy of the cell.

The cell information acquisition unit may acquire an area increase rate of a colony of the cells as the information relating to the proliferation rate. The determination unit may determine the degree of differentiation or the degree of malignancy of the cell based on the area increase rate.

The cell information acquisition unit may acquire a proliferation rate of an individual cell in a colony of the cells as the information relating to the proliferation rate. The determination unit may determine the degree of differentiation or the degree of malignancy of the cell based on the proliferation rate of the individual cell.

The cell information acquisition unit may acquire a movement distance of an individual cell in a colony of the cells as the information relating to the movement distance. The determination unit may determine the degree of differentiation or the degree of malignancy of the cell based on the movement distance of the individual cell.

The cell determination device according to the invention may further comprise a maturity degree information acquisition unit that acquires information relating to the degree of maturity of the cell, and the determination unit may change a threshold value when performing the determination according to the information relating to the degree of maturity.

The cell determination device according to the invention may further comprise a maturity degree information acquisition unit that acquires information relating to the degree of maturity of the cell, and the determination unit may assign weights to the information relating to the proliferation rate and the information relating to the movement distance according to the information relating to the degree of maturity to perform the determination.

The information relating to the degree of maturity may be information about a culture period.

The cell determination device according to the invention may further comprise a positional information acquisition unit that acquires positional information in a colony of the cells, and the determination unit may change a threshold value when performing the determination according to the positional information.

The cell determination device according to the invention may further comprise a positional information acquisition unit that acquires positional information in a colony of the cells, and the determination unit may assign weights to the information relating to the proliferation rate and the information relating to the movement distance according to the positional information to perform the determination.

The cell determination device according to the invention may further comprise a type information acquisition unit that acquires type information of the cell, and the determination unit may change a threshold value when performing the determination according to the type information.

The cell determination device according to the invention may further comprise a type information acquisition unit that acquires type information of the cell, and the determination unit may assign weights to the information relating to the proliferation rate and the information relating to the movement distance according to the type information to perform the determination.

The cell determination device according to the invention may further comprise an image pick-up controller that controls image pick-up conditions of the plurality of images, and the image pick-up controller may change the image pick-up conditions in a next image pick-up operation and subsequent image pick-up operations according to a determination result in the determination unit.

The cell determination device according to the invention may further comprise a type information acquisition unit that acquires type information of the cell; and an image pick-up controller that controls image pick-up conditions of the plurality of images, and the image pick-up controller may change an image pick-up interval of the plurality of images according to the type information of the cell.

The cell determination device according to the invention may further comprise a maturity degree information acquisition unit that acquires information relating to the degree of maturity of the cell; and an image pick-up controller that controls image pick-up conditions of the plurality of images, and the image pick-up controller may change an image pick-up interval of the plurality of images according to the information relating to the degree of maturity of the cell.

According to the invention, there is provided a cell determination method using the cell determination device comprising: acquiring information relating to a proliferation rate of a cell and information relating to a movement distance of the cell per unit time based on a plurality of cell images obtained by imaging the cell in a time series manner; and determining a state of the cell based on the information relating to the proliferation rate and the information relating to the movement distance.

According to the invention, there is provided a non-transitory computer readable recording medium recorded with a cell determination program that causes a computer to function as the cell determination device comprising: a cell information acquisition unit that acquires information relating to a proliferation rate of a cell and information relating to a movement distance of the cell per unit time based on a plurality of cell images obtained by imaging the cell in a time series manner; and a determination unit that determines a state of the cell based on the information relating to the proliferation rate and the information relating to the movement distance.

According to the cell determination device, the cell determination method, and the non-transitory computer readable recording medium recorded with the cell determination program of the invention, since information relating to a proliferation rate of a cell and information relating to a movement distance of the cell per unit time are acquired based on plural of cell images obtained by imaging the cell in a time series manner and a state of the cell is determined based on both of the information relating to the proliferation rate and the information relating to the movement distance, it is possible to prevent erroneous determination as in a case where the determination is performed based on only the movement amount of the cell as described above, and thus, to objectively determine the state of the cell with high accuracy.

DESCRIPTION OF THE PREFERRED EMBODIMENTS

Figure 1:
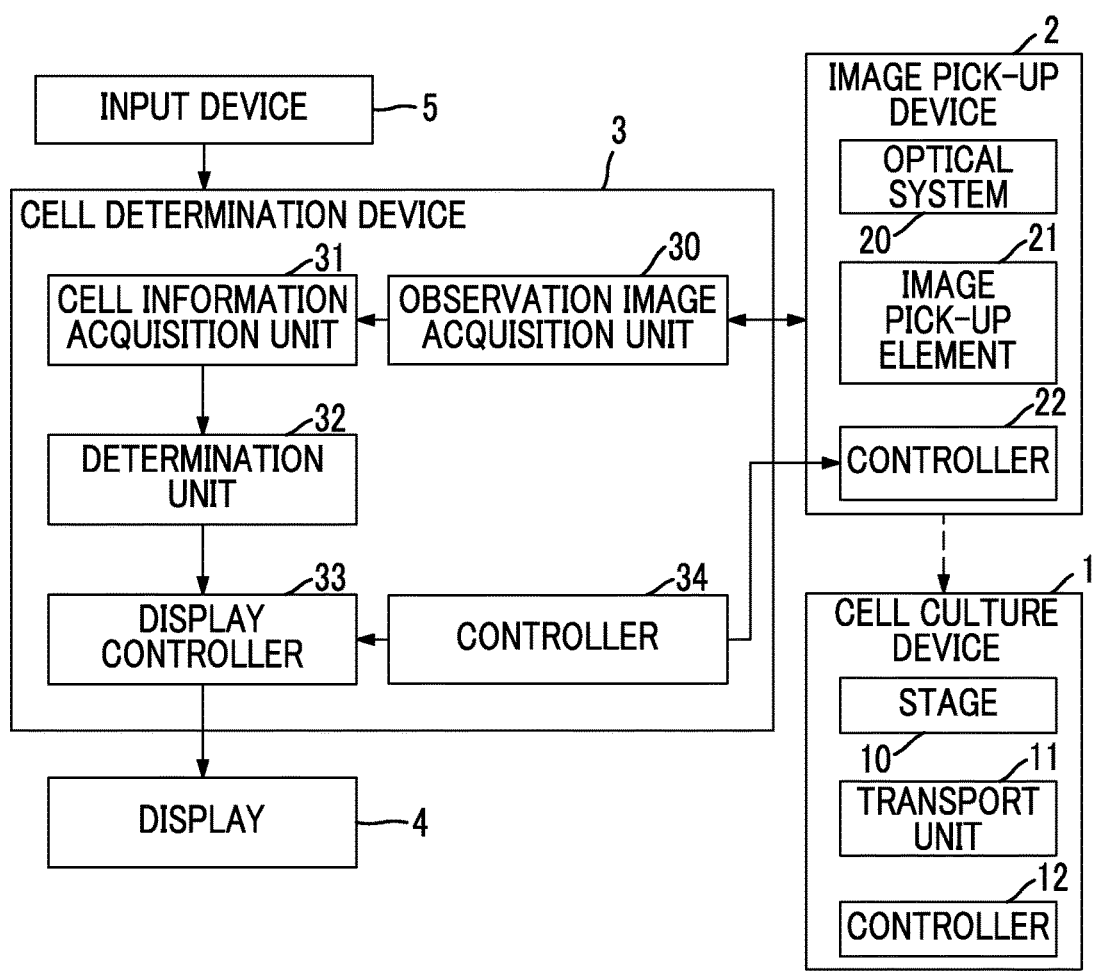
FIG. 1 is a block diagram showing a schematic configuration of a stem cell culture observation system using a cell determination device according to an embodiment of the invention.

Hereinafter, a cell culture observation system using a cell determination device according to an embodiment, a cell determination method, and a non-transitory computer readable recording medium recorded with a cell determination program of the invention will be described in detail with reference to the accompanying drawings. First, an overall configuration of a stem cell culture observation system including the cell determination device according to an embodiment of the invention will be described. FIG. 1 is a block diagram showing a schematic configuration of the cell culture observation system.

As shown in FIG. 1, the cell culture observation system includes a cell culture device 1, an image pick-up device 2, a cell determination device 3, a display 4, and an input device 5.

The cell culture device 1 is a device for performing culture of cells. As culture target cells, for example, there are stem cells such as iPS cells or ES cells, cells such as nerves, skin or cardiac muscles differentiated and induced from stem cells, cancer cells, or the like. Plural culture vessels in which culture target cells are seeded in a culture medium are accommodated in the cell culture device 1. Further, the cell culture device 1 includes a stage 10, a transport unit 11, and a controller 12.

The stage 10 is a place where a culture vessel which is an image pick-up target of the image pick-up device 2 is provided. Further, the transport unit 11 selects a culture vessel which is an image pick-up target from plural culture vessels which are accommodated in predetermined positions in the cell culture device 1, and transports the selected culture vessel to the stage 10. Furthermore, the controller 12 generally controls the cell culture device 1, and controls environmental conditions such as a temperature, a humidity, or a $CO_2$ concentration in the cell culture device 1, in addition to an operation of the stage 10 or the transport unit 11. As a configuration for adjusting the temperature, the humidity, or the $CO_2$ concentration, a known configuration may be used.

The image pick-up device 2 captures images of cells in a culture vessel provided in the stage 10 in a time series manner. The image pick-up device 2 includes an optical system 20 for forming and acquiring an image of cells, an image pick-up element 21 that photoelectrically converts the image formed by the optical system 20 to output the result as an image signal, and a controller 22 that controls the optical system 20 and the image pick-up element 21.

As the optical system 20, a phase contrast microscope or a differential interface microscope may be used, for example. Further, as the image pick-up element 21, a complementary metal-oxide semiconductor (CMOS) sensor, a charge-coupled device (CCD) sensor, or the like may be used.

The controller 22 generally controls the image pick-up device 2. Particularly, in this embodiment, the controller 22 controls an image pick-up interval of images captured in a time series manner. As a method for controlling the image pick-up interval, for example, a method for controlling a frame rate of the image pick-up element 21 may be used.

The cell determination device 3 is a computer in which a cell determination program according to an embodiment of the invention is installed.

The cell determination device 3 includes a central processing unit, a semiconductor memory, a hard disk, and the like. The cell determination program according to the embodiment of the invention is installed in the hard disk. Further, as the cell determination program is executed by a controller 34 having a central processing unit, an observation image acquisition unit 30, a cell information acquisition unit 31, a determination unit 32, and a display controller 33 as shown in FIG. 1 are operated.

The observation image acquisition unit 30 acquires plural observation images captured in a time series manner in the image pick-up device 2, and stores the acquired observation images. Further, the observation image acquisition unit 30 outputs the acquired observation images to the cell information acquisition unit 31 and the display controller 33.

The cell information acquisition unit 31 acquires at least one of information relating to a proliferation rate of a cell or information relating to a movement distance of the cell per unit time, based on the plural observation images captured in a time series manner.

As a method for acquiring the information relating to the proliferation rate of the cell, for example, a method for counting the number of cells in unit area included in observation images captured at different time points, respectively, and calculating a proliferation rate based on an increment of the number of cells and an image pick-up interval may be used. Further, a method for counting the number of cells in a cell colony included in observation images captured at different time points respectively, and calculating a proliferation rate based on an increment of the number of cells and an image pick-up interval may be used.

Further, instead of directly calculating the cell proliferation rate as described above, for example, a method for calculating areas of cell colonies included in observation images captured at different time points, respectively, and acquiring an area increase rate as the information relating to the proliferation rate may be used.

Furthermore, with respect to the information relating to the movement distance of the cell per unit time, for example, a method for detecting individual cells included in observation images or in a cell colony in the observation images and calculating a statistic value such as an average value, a maximum value, a minimum value, or the like of movement distances of individual cells may be used.

With respect to a method for detecting cells, for example, a method for detecting edges of a cell and detecting individual cells using pattern matching or the like, a method for detecting a nucleus or a nucleolus in a cell to detect individual cells, or other known techniques may be used.

With respect to association of individual cells in observation images captured at different time points, for example, a method for associating cells having similar shapes, which are present in a predetermined range may be used. As the association of the individual cells, other known techniques may be used.

The determination unit 32 determines states of cells in observation images, based on the information relating to the proliferation rate of the cell and the information relating to the movement distance of the cell acquired by the cell information acquisition unit 31.

Specifically, the determination unit 32 determines the degree of differentiation or the degree of malignancy of a cell, the type of a cancer cell, or the like as a cell state. As the degree of differentiation, a method for determining whether a cell is in an undifferentiated state or in a differentiated state may be used, or a method for classifying the degree of differentiation into plural stages and determining which stage a cell belongs to may be used. As the degree of malignancy, for example, a method for determining whether the degree of malignancy is low, intermediate, or high may be used. Further, as the type of the cancer cell, a method for determining whether the cancer cell is a proliferating cancer cell or a metastatic cancer cell may be used. A determination result in the determination unit 32 is output to the display controller 33. A specific determination method in the determination unit 32 based on the information relating to the cell proliferation rate and the information relating to the movement distance will be described in detail later.

The display controller 33 causes the display 4 to display an observation image acquired by the observation image acquisition unit 30, or causes the display 4 to display a determination result in the determination unit 32. Further, the display controller 33 may cause the display 4 to display the information relating to the cell proliferation and the information relating to the movement distance used in the determination, in addition to the determination result.

The controller 34 generally controls the cell determination device 3 as a whole. Particularly, the controller 34 of this embodiment outputs a control signal to the controller 22 of the image pick-up device 2 so that an image pick-up interval of observation images in a next image pick-up operation and subsequent image pick-up operations is changed according to the determination result in the determination unit 32. In this embodiment, the controller 34 corresponds to an image pick-up controller.

The input device 5 includes a mouse, a keyboard, or the like, and receives various setting inputs from a user.

Figure 2:
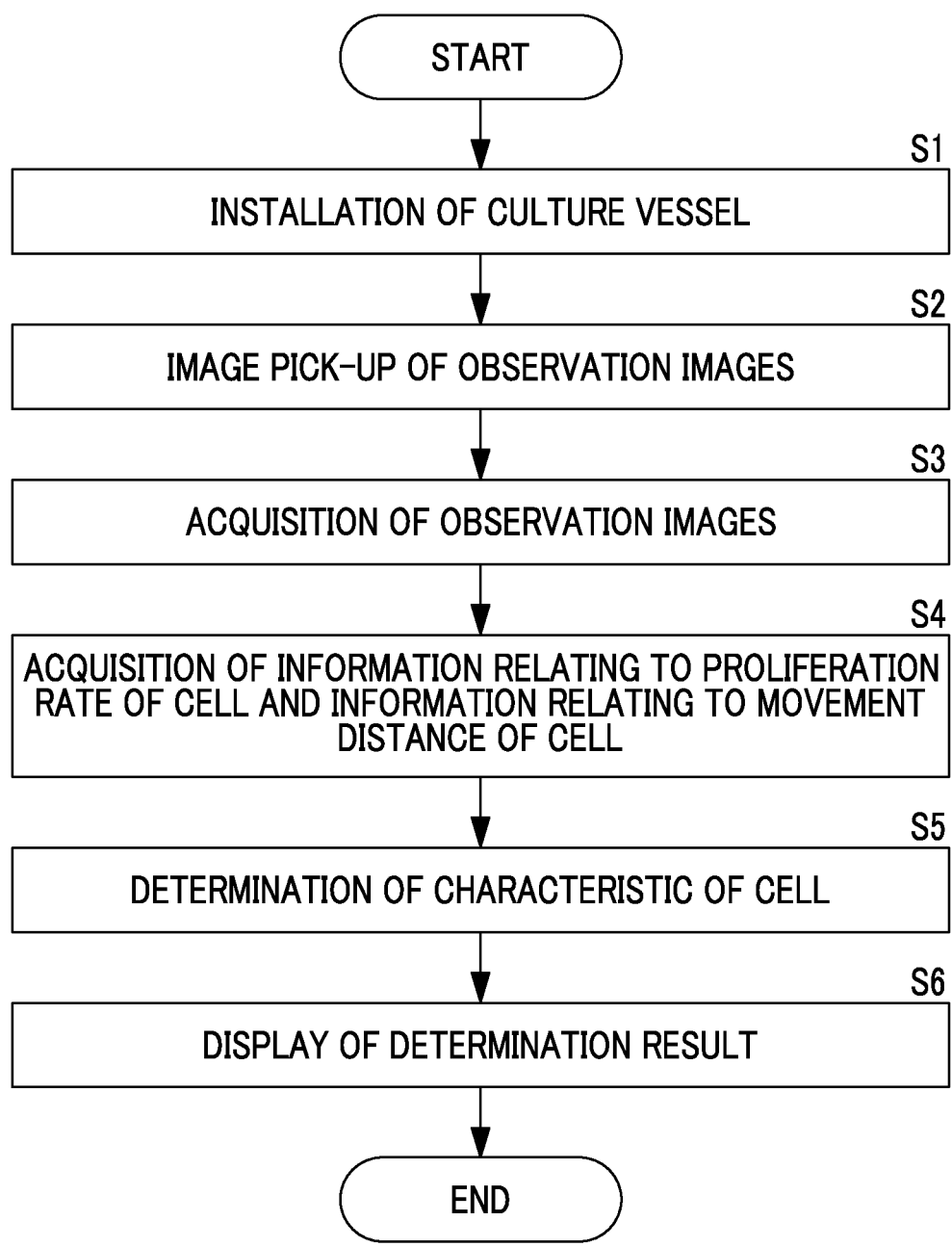
FIG. 2 is a flowchart illustrating an operation of the stem cell culture observation system using a cell image pick-up control device according to an embodiment of the invention.

Next, an operation of the above-described stem cell culture observation system will be described with reference to the flowchart shown in FIG. 2.

First, in the cell culture device 1, a culture vessel which is an image pick-up target is selected from plural accommodated culture vessels by the transport unit 11, and the selected culture vessel is installed in the stage 10 (S1).

Figure 3:
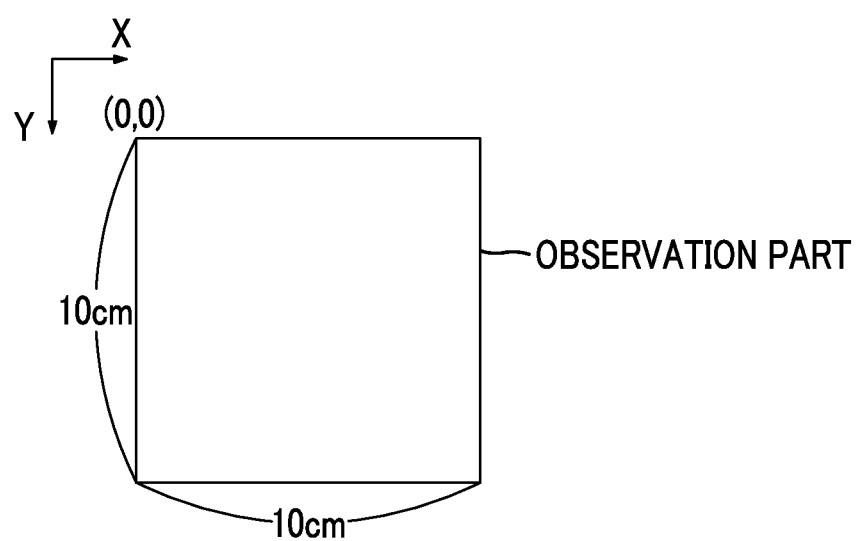
FIG. 3 is a diagram illustrating an example of a cell observation part.

Further, image pick-up of observation images in an observation part including a stem cell in the culture vessel is performed using a phase contrast microscope or a differential interference microscope of the image pick-up device 2 in a time series manner (S2). Specifically, a rectangular observation part of 10 cm×10 cm as shown in FIG. 3 is imaged by 40 shots×40 shots using the phase contrast microscope to obtain one observation image.

Observation images captured by the image pick-up device 2 in a time series manner are output to the cell determination device 3, and are acquired by the observation image acquisition unit 30 of the cell determination device 3 (S3).

The plural observation images acquired by the observation image acquisition unit 30 are output to the cell information acquisition unit 31. The cell information acquisition unit 31 acquires information relating to a proliferation rate of a cell and information relating to a movement distance of the cell as described above, based on the input plural observation images (S4).

The information relating to the proliferation rate and the information relating to the movement distance acquired by the cell information acquisition unit 31 are output to the determination unit 32. The determination unit 32 determines the degree of differentiation, the degree of malignancy of a cell, or the like in an observation image, based on the information (S5).

A determination result in the determination unit 32 is output to the display controller 33. The display controller 33 causes the display 4 to display the input determination result and an observation image which is a determination target (S6).

Figure 4:
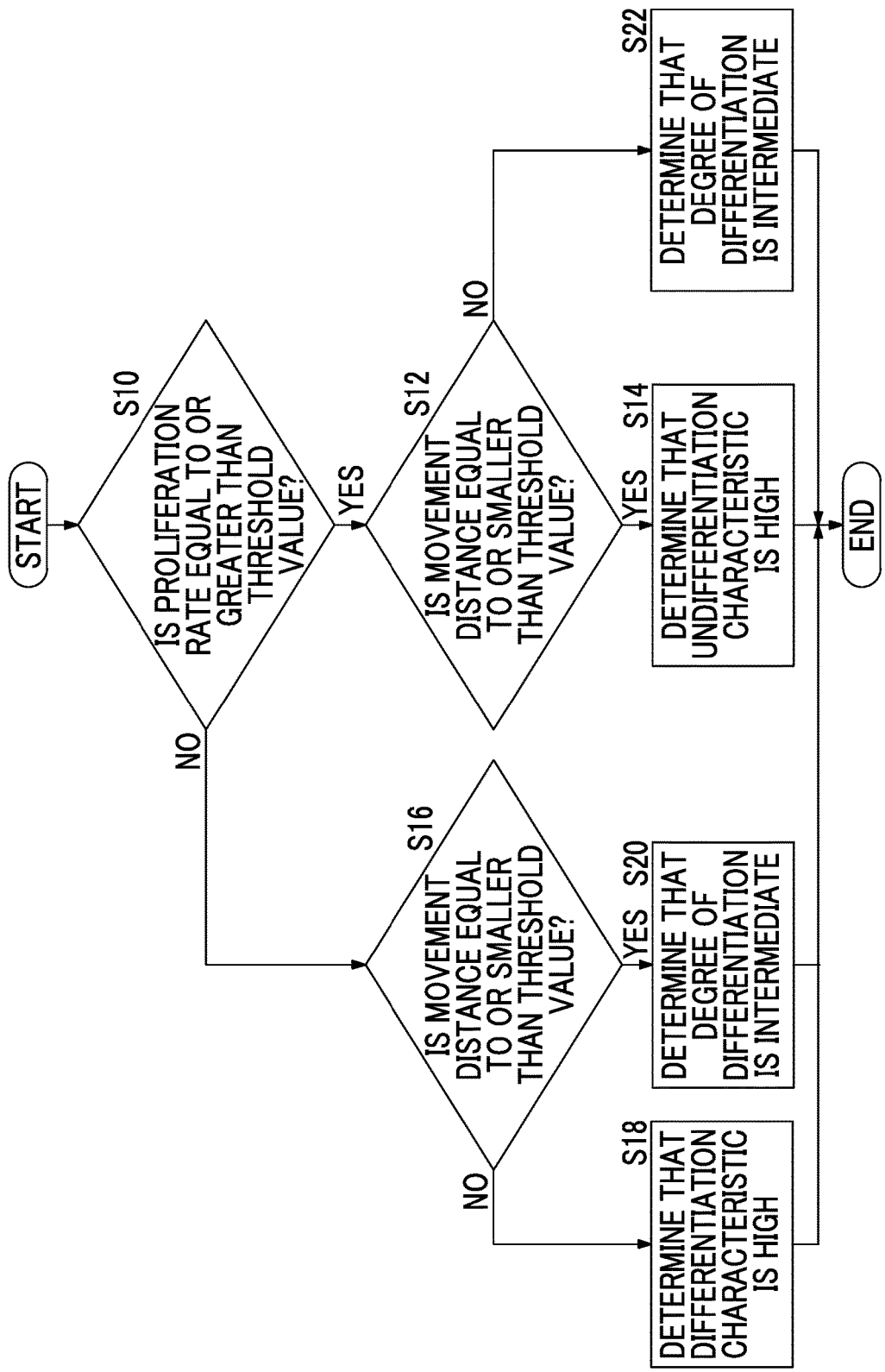
FIG. 4 is a flowchart illustrating a method for determining the degree of differentiation of a stem cell.
Figure 5:
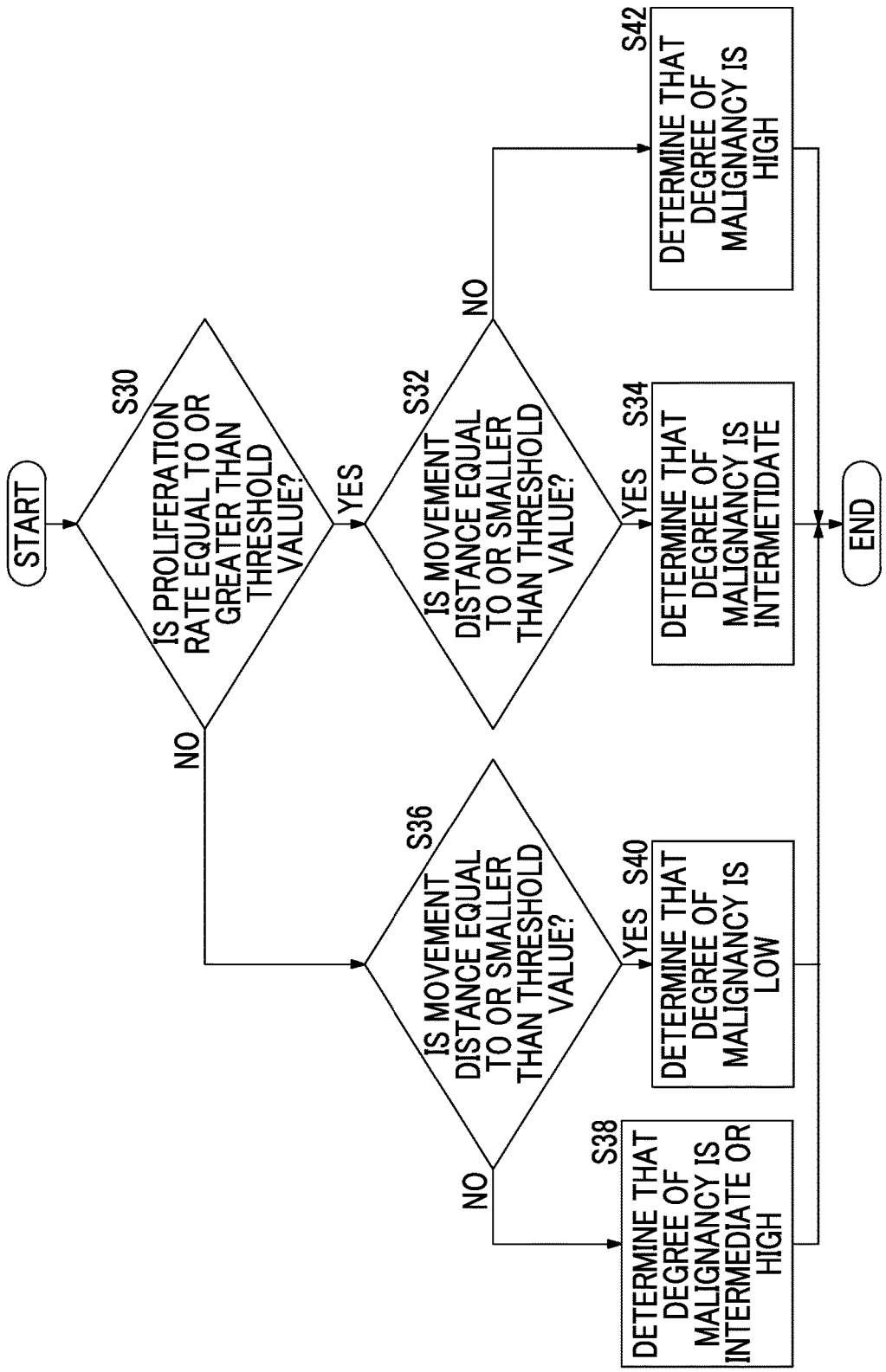
FIG. 5 is a flowchart illustrating a method for determining the degree of malignancy of a cancer cell.
Figure 6:
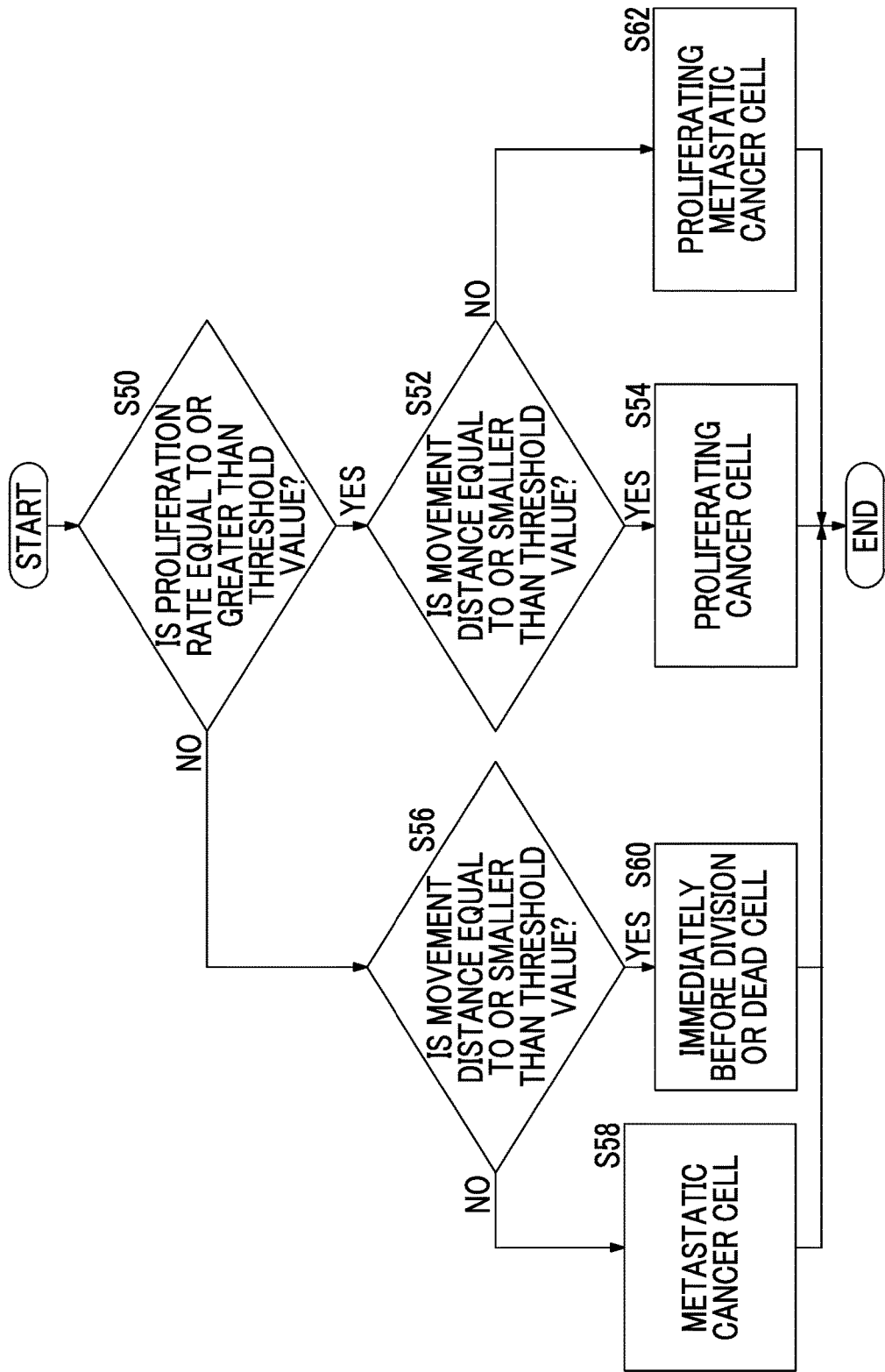
FIG. 6 is a flowchart illustrating a method for determining a state of a cancer cell.

Next, a specific determination method in the determination unit 32 of the cell determination device 3 will be described in detail with reference to flowcharts shown in FIGS. 4 to 6.

First, a method for determining the degree of differentiation of stem cells such as iPS cells or ES cells will be described with reference to the flowchart of FIG. 4, using the information relating to the proliferation rate of the cell and the information relating to the movement distance of the cell. The following determination method is a determination method based on a viewpoint that an undifferentiated cell has a high proliferation rate and a short movement distance but a differentiated cell has a low proliferation rate and a long movement distance.

The determination unit 32 first determines whether a proliferation rate of a cell is equal to or greater than a predetermined threshold value (S10). In a case where the proliferation rate of the cell is equal to or greater than the threshold value (YES in S10), it is determined whether a movement distance of the cell is equal to or smaller than a threshold value (S12). Further, in a case where it is determined that the movement distance of the cell is equal to or smaller than the threshold value (YES in S12), it is determined that an undifferentiation characteristic of the cell is high (S14).

As the determination of the threshold value of the proliferation rate, for example, a method for determining whether the cell is divided once or more a day, for example, may be used. Further, in a case where the above-described area increase rate is acquired as the information relating to the proliferation rate, for example, a method for determining whether the area becomes two times or more a day may be used. In addition, as the determination of the threshold value of the movement distance, a method for determining whether a statistic value of the movement distance a day is 50 μm or greater and 1000 μm or smaller may be used.

In a case where it is determined in S10 that the proliferation rate of the cell is smaller than the threshold value (NO) and it is determined in S16 that the movement distance of the cell is larger than the threshold value (NO), it is determined that a differentiation characteristic of the cell is high (S18).

In a case where it is determined in S16 that the movement distance of the cell is equal to or smaller than the threshold value (YES), and in a case where it is determined in S12 that the movement distance is larger than the threshold value (NO), it is determined that the degree of differentiation is intermediate (S20 and S22).

As described above, by determining the degree of differentiation using both of the information relating to the proliferation rate of the cell and the information relating to the movement distance of the cell, it is possible to perform determination with higher accuracy.

Next, a method for determining the degree of malignancy of a cancer cell using the information relating to the cell proliferation rate of the cell and the information relating to the movement distance of the cell will be described with reference to the flowchart of FIG. 5.

First, the determination unit 32 determines whether a proliferation rate of a cell is equal to or greater than a predetermined threshold value (S30). In a case where it is determined that the proliferation rate of the cell is equal to or greater than the threshold value (YES in S30), the determination unit 32 determines whether a movement distance of the cell is equal to or smaller than a threshold value (S32). Further, in a case where it is determined that the movement distance of the cell is larger than the threshold value (NO in S32), the determination unit 32 determines that the degree of malignancy is high due to a high metastatic characteristic and the progress of proliferation (S42).

In a case where it is determined in S30 that the proliferation rate of the cell is equal to or greater than the threshold value (YES), and in a case where it is determined in S32 that the movement distance of the cell is equal to or smaller than the threshold value (YES), the determination unit 32 determines that the cancer cell is a general proliferating cancer cell, and thus, it is determined that the degree of malignancy is intermediate (S34).

In a case where it is determined in S30 that the proliferation rate of the cell is smaller than the threshold value (NO), and in a case where it is determined in S36 that the movement distance of the cell is longer than the threshold value (NO), the determination unit 32 determines that the cancer cell is a metastatic cancer cell, and thus, it is determined that the degree of malignancy is intermediate or high (S38). The "intermediate or high" means that the degree of malignancy is higher than that of the "intermediate" determined in S34.

In a case where it is determined in S30 that the proliferation rate of the cell is smaller than the threshold value (NO), and in a case where it is determined in S36 that the movement distance of the cell is equal to or shorter than the threshold value (YES), it is estimated that the cell is dead, is in a non-divided state, or is in a state where proliferation is hindered due to an agent or the like, and thus, it is determined that the degree of malignancy is low (S40).

As described above, by determining the degree of malignancy using both of the information relating to the proliferation rate of the cell and the information relating to the movement distance of the cell, it is possible to perform determination with higher accuracy.

Then, a method for determining the type of a cancer cell using the information relating to the proliferation rate of the cell and the information relating to the movement distance of the cell will be described with reference to the flowchart of FIG. 6. The following determination method is a determination method based on a viewpoint that a cancer cell having a high proliferation rate and a short movement distance is highly likely to be a proliferating cancer cell, and a viewpoint that a cancer cell having a low proliferation rate (for example, a case where time necessary for one division is two days) and a long movement distance (1 mm/day) is a metastatic cancer cell.

The determination unit 32 first determines whether a proliferation rate of a cell is equal to or greater than a predetermined threshold value (for example, one or more divisions a day) (S50). In a case where the proliferation rate of the cell is equal to or greater than the threshold value (YES in S50), the determination unit 32 determines whether a movement distance of the cell is equal to or shorter than a threshold value (for example, 0.1 mm/day or shorter) (S52). Further, in a case where it is determined that the movement distance of the cell is equal to or shorter than the threshold value (YES in S52), the determination unit 32 determines that the cancer cell is a proliferating cancer cell (S54).

In a case where it is determined in S50 that the proliferation rate of the cell is equal to or greater than the threshold value (YES) and in a case where it is determined in S52 that the movement distance of the cell is greater than the threshold value (NO), the determination unit 32 determines that the cancer cell is a metastatic proliferating cancer cell (S62).

In a case where it is determined in S50 that the proliferation rate of the cell is smaller than the threshold value (NO) and in a case where it is determined in S56 that the movement distance of the cell is greater than the threshold value (NO), the determination unit 32 determines that the cancer cell is a metastatic cancer cell (S58).

Further, in a case where it is determined in S56 that the movement distance of the cell is equal to or shorter than the threshold value (YES), it is determined that the cancer cell is a dead cell or a cell immediately before division (S60).

As described above, by determining the type of the cancer cell using both of the information relating to the proliferation rate of the cell and the information relating to the movement distance of the cell, it is possible to perform determination with higher accuracy.

Further, in the above description, the determination unit 32 performs the threshold value determination with respect to the information relating to the proliferation rate of the cell and the information relating to the movement distance of the cell to determine the degree of differentiation and the degree of malignancy, but the threshold values used in the determination may be changed.

Figure 7:
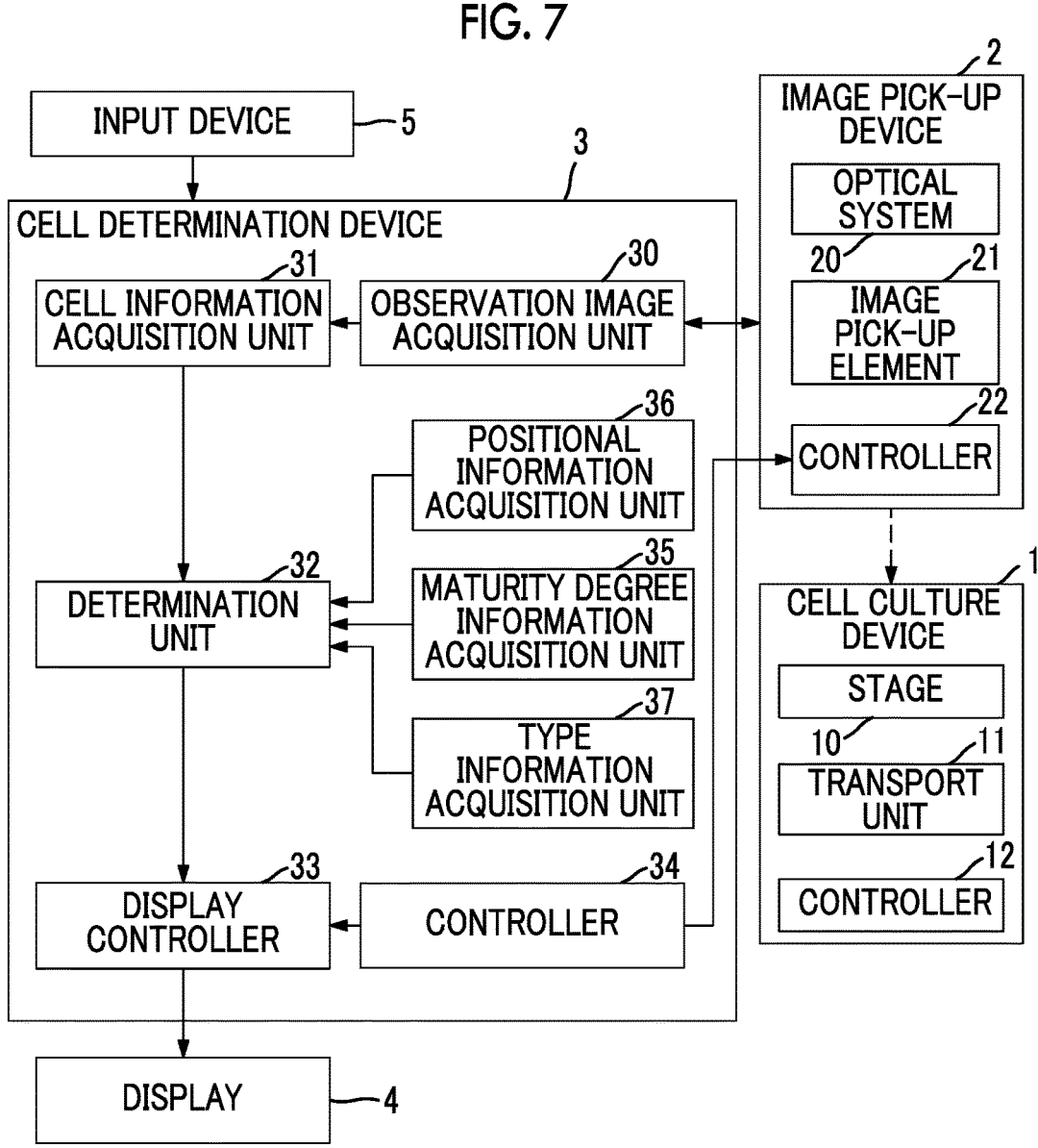
FIG. 7 is a block diagram showing a schematic configuration of a stem cell culture observation system using the cell determination device according to another embodiment of the invention.
Figure 8:
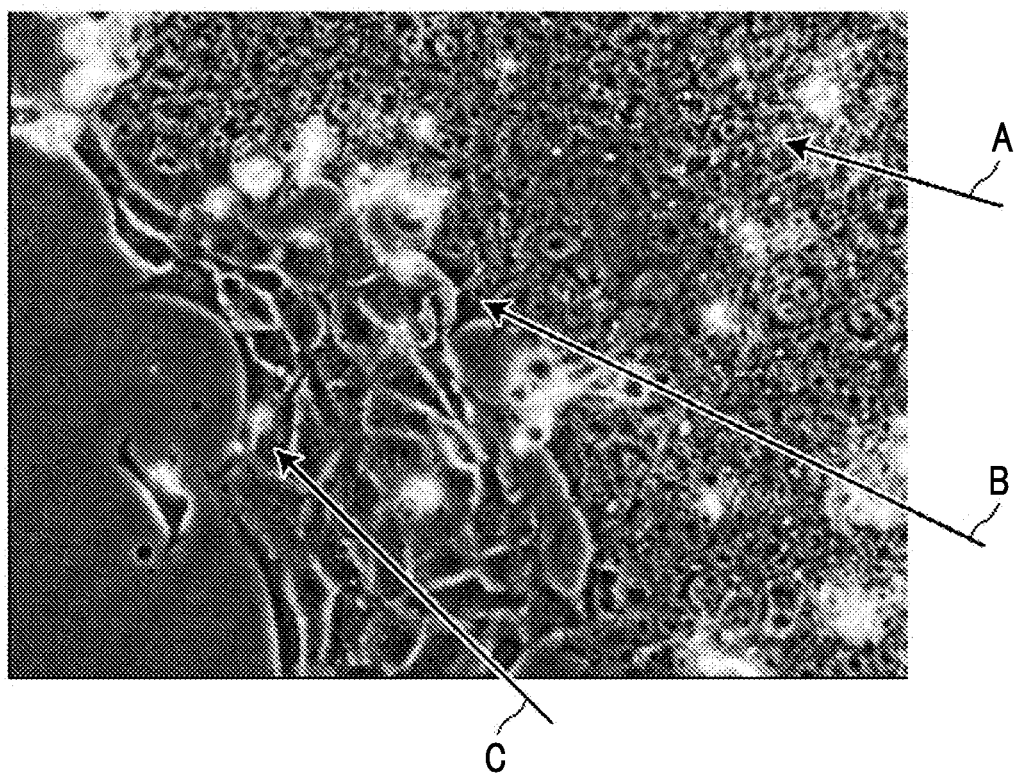
FIG. 8 is a diagram illustrating a problem in a case where state determination based on a still image of a cell is performed.

Specifically, for example, a maturity degree information acquisition unit 35 that acquires information relating to the degree of maturity of a cell which is an image pick-up target may be provided as shown in FIG. 7, and the threshold values may be changed based on the information relating to the degree of maturity. As the information relating to the degree of maturity, for example, information about a culture period of a cell may be used. The information about the culture period may be set and input using the input device 5 from a user, or may be set by measuring a time elapsed after a cell is seeded to a culture plate using a timer or the like.

Further, the information relating to the degree of maturity is not limited to the culture period, and for example, the size of a cell colony may be acquired as the information relating to the degree of maturity. That is, any type of information that is changed according to the degree of maturity of a cell may be used as the information relating to the degree of maturity.

Furthermore, as a method for changing the threshold value of the information relating to the proliferation rate based on the information relating to the degree of maturity, in a case where the threshold value determination is performed such that the undifferentiation characteristic is high in a case where the information relating to the proliferation rate is equal to or greater than the threshold value and the differentiation characteristic is high in a case where the information relating to the proliferation rate is smaller than the threshold value, a method for changing the threshold value to become larger as the culture period is longer may be used. Further, as a method for changing the threshold value of the information relating to the movement distance, in a case where the threshold value determination is performed such that the undifferentiation characteristic is high in a case where the information relating to the movement distance is equal to or smaller than the threshold value and the differentiation characteristic is high in a case where the information relating to the movement distance is larger than the threshold value, a method for changing the threshold value to become larger as the culture period is longer may be used. With respect to the threshold value corresponding to the information relating to the degree of maturity, a table for associating the information relating to the degree of maturity with the threshold value may be provided with respect to the determination unit 32, and the threshold value may be acquired with reference to the table.

In addition, in the above description, the degree of differentiation and the degree of malignancy is determined by performing the threshold value determination with respect to the information relating to the proliferation rate and the information relating to the movement distance, but a weight may be respectively assigned to a result of the threshold value determination with respect to the information relating to the proliferation rate and a result of the threshold value determination with respect to the information relating to the movement distance to perform a weighting operation. Further, operation results may be acquired as evaluation values, and the degree of differentiation and the degree of malignancy may be determined based on the evaluation values.

For example, with respect to the information relating to the proliferation rate, in a case where the proliferation rate is equal to or greater than the threshold value, the evaluation result is set to "2", and in a case where the proliferation rate is smaller than the threshold value, the evaluation result is set to "1". Further, with respect to the information relating to the movement distance, for example, in a case where the movement distance is equal to or greater than the threshold value, the evaluation result is set to "1", and in a case where it is smaller than the threshold value, the evaluation result is set to "2". In this way, by performing the weighting operation with respect to the evaluation result of the information relating to the proliferation rate and the evaluation result of the information relating to the movement distance, a final evaluation value may be acquired. Further, the degree of differentiation and the degree of malignancy may be determined based on the magnitude of the evaluation value. In a case where the evaluation results are set as described above, it may be determined that the undifferentiation characteristic becomes higher as the evaluation value becomes larger.

Further, when the evaluation value is calculated through the weighting operation as described above, the weights may be changed according to the information relating to the above-mentioned degree of maturity.

Specifically, for example, the weights may be changed so that a ratio of a weighting coefficient to the evaluation result of the information relating to the movement distance to a weighting coefficient to the evaluation result of the information relating to the proliferation rate becomes larger as the culture period becomes longer. Contrarily, the weights may be changed so that the ratio of the weighting coefficient to the evaluation result of the information relating to the movement distance to the weighting coefficient to the evaluation result of the information relating to the proliferation rate becomes smaller as the culture period becomes longer.

Further, as shown in FIG. 7, a positional information acquisition unit 36 that acquires positional information in a cell colony of cells which are determination targets may be provided, and the threshold values may be changed based on the positional information. The positional information may be set and input using the input device 5 from a user, for example.

Furthermore, as a method for changing the threshold value of the information relating to the proliferation rate based on positional information about a cell which is a determination target in a cell colony, in a case where the threshold value determination is performed such that the undifferentiation characteristic is high in a case where the information relating to the proliferation rate is equal to or greater than the threshold value and the differentiation characteristic is high in a case where the information relating to the proliferation rate is smaller than the threshold value, a method for setting a threshold value in a case where the positional information about the cell which is the determination target corresponds to a peripheral portion of the cell colony to be smaller than a threshold value in a case where the positional information about the cell which is the determination target corresponds to a central portion of the cell colony, may be used. In addition, as a method for changing the threshold value of the information relating to the movement distance, in a case where the threshold value determination is performed such that the undifferentiation characteristic is high in a case where the information relating to the movement distance is equal to or smaller than the threshold value and the differentiation characteristic is high in a case where the information relating to the movement distance is larger than the threshold value, a method for setting a threshold value in a case where the positional information about the cell which is the determination target corresponds to a peripheral portion of the cell colony to be larger than a threshold value in a case where the positional information about the cell which is the determination target corresponds to a central portion of the cell colony, may be used. With respect to the threshold value corresponding to the positional information about the cell which is the determination target, a table for associating the positional information with the threshold value may be provided with respect to the determination unit 32, and the threshold value may be acquired with reference to the table.

As described above, in a case where the weighting operation is performed with respect to the evaluation result of the information relating to the proliferation rate and the evaluation result of the information relating to the movement distance to acquire the evaluation value, the weights may be changed according to the above-described positional information.

Specifically, for example, a method for changing the ratio of the weighting coefficient to the evaluation result of the information relating to the movement distance to the weighting coefficient to the evaluation result of the information relating to the proliferation rate to become larger in a case where the positional information corresponds to the peripheral portion of the cell colony compared with a case where the positional information correspond to the central portion of the cell colony, may be used. Further, contrarily, a method for changing the ratio of the weighting coefficient to the evaluation result of the information relating to the movement distance to the weighting coefficient to the evaluation result of the information relating to the proliferation rate to become smaller in a case where the positional information corresponds to the peripheral portion of the cell colony compared with a case where the positional information correspond to the central portion of the cell colony, may be used.

As shown in FIG. 7, a type information acquisition unit 37 that acquires information indicating the type of a cell which is a determination target may be provided, and a threshold value may be changed based on the type information. The type information may be set and input using the input device 5 from a user, for example.

Further, as a method for changing the threshold value of the information relating to the proliferation rate based on the information indicating the type of the cell, in a case where the threshold value determination is performed such that the undifferentiation characteristic is high in a case where the information relating to the proliferation rate is equal to or greater than the threshold value and the differentiation characteristic is high in a case where the information relating to the proliferation rate is smaller than the threshold value, a method for setting a threshold value in a case where the cell which is the determination target is a cell of which the proliferation rate is relatively fast to be larger than a threshold value in a case where the cell which is the determination target is a cell of which the proliferation rate is relatively slow, may be used. With respect to a threshold value corresponding to the type of the cell which is the determination target, a table for associating the information indicating the type of the cell with the threshold value may be provided with respect to the determination unit 32, and the threshold value may be acquired with reference to the table.

Furthermore, as described above, in a case where the weighting operation is performed with respect to the evaluation result of the information relating to the proliferation rate and the evaluation result of the information relating to the movement distance to acquire the evaluation value, the weights may be changed according to the above-described information indicating the type of the cell.

Specifically, for example, in a case where the cell which is the determination target is a stem cell before differentiation and induction, a weighting coefficient to the evaluation result of the information relating to the proliferation rate and a weighting coefficient to the evaluation result of the information relating to the movement distance are set to have the same value. In a case where the cell which is the determination target is a cardiac muscle cell after differentiation and induction, since the cardiac muscle cell is not divided, the weighting coefficient to the evaluation result of the information relating to the proliferation rate may be set to 0 (zero), and the weighting coefficient to the evaluation result of the information relating to the movement distance may be set to a predetermined value.

In this way, by changing the weighting coefficients according to characteristics of the cells which are the determination targets, it is possible to determine the degree of differentiation with higher accuracy.

Hereinbefore, an example of a specific determination method in the determination unit 32 of the cell determination device 3 has been described.

Further, in the cell culture observation system of this embodiment, plural observation images captured in a time series manner are acquired as described above, but an image pick-up interval when acquiring the plural observation images may be changed. The image pick-up interval may be controlled by the controller 22 of the image pick-up device 2 based on a control signal from the controller 34 of the cell determination device 3 as described above.

Specifically, an image pick-up interval in a next image pick-up operation and subsequent image pick-up operations may be changed according to a determination result in the determination unit 32 of the cell determination device 3. For example, when determining the degree of differentiation of a stem cell by the determination unit 32, in a case where it is determined by the determination unit 32 that the undifferentiation characteristic is high or the degree of differentiation is intermediate, since an image pick-up interval may be set according to a cell cycle of the stem cell, the image pick-up interval may be set to a long image pick-up interval of an order of several hours. At a time point where it is determined by the determination unit 32 that the differentiation characteristic is high and thereafter, for example, in a case where the stem cell is differentiated and induced to a nerve axon, a cardiac muscle, or the like, the image pick-up interval may be changed to a short image pick-up interval of an order of several milliseconds according to a growth rate of the nerve axon or a pulsation of the cardiac muscle.

Further, an optical magnification may be changed, for example, in addition to the image pick-up interval. That is, at a time point where it is determined that the differentiation characteristic is high and thereafter, the optical magnification may be changed to a low magnification. The optical magnification of an observation image may be similarly controlled by the controller 22 of the image pick-up device 2 based on a control signal from the controller 34 of the cell determination device 3 as described above.

In addition, the image pick-up interval may be changed according to the type of a cell acquired by the above-described type information acquisition unit 37. For example, when determining the degree of differentiation of a stem cell or the degree of malignancy of a cancer cell by the determination unit 32, the image pick-up interval may be set to be shorter as the stem cell or the cancer cell has a relatively faster growth rate.

Further, the image pick-up interval may be changed according to the information relating to the degree of maturity acquired by the above-described maturity degree information acquisition unit 35. For example, in a case where the degree of differentiation of a stem cell or the degree of malignancy of a cancer cell is determined by the determination unit 32, the image pick-up interval may be changed according to a culture period. For example, the image pick-up interval may be set to become longer as the culture period becomes longer. Further, contrarily, the image pick-up period may be set to become shorter as the culture period becomes longer. Whether to determine the image pick-up interval to become longer or shorter according to the culture period may be automatically determined based on the type of the cell or the content of determination, or may be set and input using the input device 5 from a user.

EXPLANATION OF REFERENCES

1: cell culture device
2: image pick-up device
3: cell determination device
4: display
5: input device
10: stage
11: transport unit
12: controller
20: optical system
21: image pick-up element
22: controller
30: observation image acquisition unit
31: cell information acquisition unit
32: determination unit
33: display controller
34: controller
35: maturity degree information acquisition unit
36: position information unit
37: type information acquisition unit

What is claimed is:

1. A cell determination device comprising:
a controller configured to
acquire information relating to a proliferation rate of a cell and information relating to a movement distance of the cell per unit time based on a plurality of cell images obtained by imaging the cell in a time series manner,
determine a state of the cell by comparing the information relating to the proliferation rate and the information relating to the movement distance with a threshold value of the proliferation rate and a threshold value of the movement distance respectively, and
acquire information relating to a culture period of the cell,
wherein the controller changes the threshold value of the proliferation rate and the threshold value of the movement distance that are used for the comparison according to the information relating to the culture period.

2. The cell determination device according to claim 1, wherein the controller determines the degree of differentiation or the degree of malignancy of the cell.

3. The cell determination device according to claim 2, wherein the controller acquires an area increase rate of a colony of the cells as the information relating to the proliferation rate.

4. The cell determination device according to claim 2, wherein the controller acquires a proliferation rate of an individual cell in a colony of the cells as the information relating to the proliferation rate.

5. The cell determination device according to claim 2, wherein the controller acquires a movement distance of an individual cell in a colony of the cells as the information relating to the movement distance.

6. The cell determination device according to claim 1, wherein the controller acquires an area increase rate of a colony of the cells as the information relating to the proliferation rate.

7. The cell determination device according to claim 1, wherein the controller acquires a proliferation rate of an individual cell in a colony of the cells as the information relating to the proliferation rate.

8. The cell determination device according to claim 1, wherein the controller acquires a movement distance of an individual cell in a colony of the cells as the information relating to the movement distance.

9. A cell determination method using the cell determination device according to claim 1 comprising:
acquiring information relating to the proliferation rate of the cell and information relating to the movement distance of the cell per unit time based on the plurality of cell images obtained by imaging the cell in a time series manner;
determining a state of the cell by comparing the information relating to the proliferation rate and the information relating to the movement distance with a threshold value of the proliferation rate and a threshold value of the movement distance respectively;
acquiring information relating to a culture period of the cell; and
changing the threshold value of the proliferation rate and the threshold value of the movement distance that are used from the comparison according to the information relating to the culture period.

10. The cell determination device according to claim 1, wherein the controller classifies a degree of differentiation of a stem cell into one of three categories depending on whether the proliferation rate is equal to or greater than the threshold value of the proliferation rate and the movement distance is equal to or smaller than the threshold value of the movement distance or the proliferation rate is smaller than the threshold value of the proliferation rate and the movement distance is equal to or smaller than the threshold value of the movement distance as the determination of the state of the cell.

11. The cell determination device according to claim 1, wherein the controller classifies a degree of malignancy of a cancer cell into one of four categories depending on whether the proliferation rate is equal to or greater than the threshold value of the proliferation rate and the movement distance is equal to or smaller than the threshold value of the movement distance or the proliferation rate is smaller than the threshold value of the proliferation rate and the movement distance is equal to or smaller than the threshold value of the movement distance as the determination of the state of the cell.

12. The cell determination device according to claim 1, wherein the controller classifies a type of a cancer cell into one of a proliferating cancer cell, a metastatic proliferating cancer cell, a metastatic cancer cell or a dead cell or a cell immediately before division depending on whether the proliferation rate is equal to or greater than the threshold value of the proliferation rate and the movement distance is equal to or smaller than the threshold value of the movement distance or the proliferation rate is smaller than the threshold value of the proliferation rate and the movement distance is equal to or smaller than the threshold value of the movement distance as the determination of the state of the cell.

13. A cell determination device comprising:
a controller configured to
acquire information relating to a proliferation rate of a cell and information relating to a movement distance of the cell per unit time based on a plurality of cell images obtained by imaging the cell in a time series manner,
determine a state of the cell based on the information relating to the proliferation rate and the information relating to the movement distance, and
acquire information relating to the degree of maturity of the cell,
wherein the controller assigns weights to the information relating to the proliferation rate and the information relating to the movement distance according to the information relating to the degree of maturity to perform the determination.

14. A cell determination device comprising:
a controller configured to
acquire information relating to a proliferation rate of a cell and information relating to a movement distance of the cell per unit time based on a plurality of cell images obtained by imaging the cell in a time series manner,
determine a state of the cell based on the information relating to the proliferation rate and the information relating to the movement distance, and
acquire positional information in a colony of the cells,
wherein the controller assigns weights to the information relating to the proliferation rate and the information relating to the movement distance according to the positional information to perform the determination.

15. A cell determination device comprising:
a controller configured to
acquire information relating to a proliferation rate of a cell and information relating to a movement distance of the cell per unit time based on a plurality of cell images obtained by imaging the cell in a time series manner,
determine a state of the cell by comparing the information relating to the proliferation rate and the information relating to the movement distance with a threshold value of the proliferation rate and a threshold value of the movement distance respectively, and
acquire type information of the cell,
wherein the controller changes the threshold value of the proliferation rate and the threshold value of the movement distance that are used for the comparison according to the type information.

16. A cell determination device comprising:
a controller configured to
acquire information relating to a proliferation rate of a cell and information relating to a movement distance of the cell per unit time based on a plurality of cell images obtained by imaging the cell in a time series manner, determine a state of the cell based on the information relating to the proliferation rate and the information relating to the movement distance, and acquire type information of the cell, wherein the controller assigns weights to the information relating to the proliferation rate and the information relating to the movement distance according to the type information to perform the determination.

17. A cell determination device comprising:

a controller configured to acquire information relating to a proliferation rate of a cell and information relating to a movement distance of the cell per unit time based on a plurality of cell images obtained by imaging the cell in a time series manner, and determine a state of the cell based on the information relating to the proliferation rate and the information relating to the movement distance; and an image pick-up controller that controls image pick-up conditions of the plurality of images, wherein the image pick-up controller changes the image pick-up conditions in a next image pick-up operation and subsequent image pick-up operations according to a determination result in the controller.

18. A cell determination device comprising:

a controller configured to acquire information relating to a proliferation rate of a cell and information relating to a movement distance of the cell per unit time based on a plurality of cell images obtained by imaging the cell in a time series manner, determine a state of the cell based on the information relating to the proliferation rate and the information relating to the movement distance, and acquire information relating to the degree of maturity of the cell; and an image pick-up controller that controls image pick-up conditions of the plurality of images, wherein the image pick-up controller changes an image pick-up interval of the plurality of images according to the information relating to the degree of maturity of the cell.

19. A non-transitory computer readable recording medium recorded with a cell determination program that causes a computer to function as the cell determination device according to claim 1 comprising:

a controller configured to acquire information relating to the proliferation rate of the cell and information relating to the movement distance of the cell per unit time based on the plurality of cell images obtained by imaging the cell in a time series manner, determine a state of the cell by comparing the information relating to the proliferation rate and the information relating to the movement distance with a threshold value of the proliferation rate and a threshold value of the movement distance respectively, and acquire information relating to a culture period of the cell, wherein the controller changes the threshold value of the proliferation rate and the threshold value of the movement distance that are used for the comparison according to the information relating to the culture period.

* * * * *